United States Patent [19]
Thornton et al.

[11] Patent Number: 5,348,017
[45] Date of Patent: Sep. 20, 1994

[54] DRIVE SHAFT FOR AN INTRAVASCULAR CATHETER SYSTEM

[75] Inventors: Peter Thornton, Cupertino; Stephen M. Salmon, Sunnyvale, both of Calif.

[73] Assignee: Cardiovascular Imaging Systems, Inc., Sunnyvale, Calif.

[21] Appl. No.: 6,226

[22] Filed: Jan. 19, 1993

[51] Int. Cl.$^5$ ............................................. A61B 8/12
[52] U.S. Cl. .............................. 128/662.06; 606/159
[58] Field of Search ............... 128/657, 772, 662.06; 606/159; 604/95–97

[56] References Cited

U.S. PATENT DOCUMENTS

| | | | |
|---|---|---|---|
| 4,998,923 | 3/1991 | Samson et al. | 606/194 |
| 5,002,058 | 3/1991 | Martinelli | 128/662.06 |
| 5,025,799 | 6/1991 | Wilson | 128/772 |
| 5,095,911 | 3/1992 | Pomeranz | 128/662.06 |
| 5,108,411 | 4/1992 | McKenzie | 606/159 |
| 5,111,829 | 5/1992 | Alvarez de Toledo | 128/772 |
| 5,143,085 | 9/1992 | Wilson | 128/772 |
| 5,147,370 | 9/1992 | McNamara et al. | 606/108 |
| 5,203,338 | 4/1993 | Jang | 128/662.06 |
| 5,243,996 | 9/1993 | Hall | 128/657 |

*Primary Examiner*—Francis Jaworski
*Attorney, Agent, or Firm*—Townsend and Townsend Khourie and Crew

[57] ABSTRACT

The present invention provides an improved drive shaft for use in a catheter system having a rotating imaging or interventional work element. A drive shaft according to the present invention is formed at least in part of a material having super elastic properties. This material provides an advantageous combination of column strength and torsional rigidity with the ability to sustain substantial bending without permanent deformation. Preferred embodiments are formed as hollow tubes to allow electrical conducting wires to be disposed within the body of the drive shaft. Some embodiments combine relatively rigid proximal segments with relatively flexible distal segments to allow for entry of the work element into narrow and twisting regions of a patient's vascular system.

18 Claims, 5 Drawing Sheets

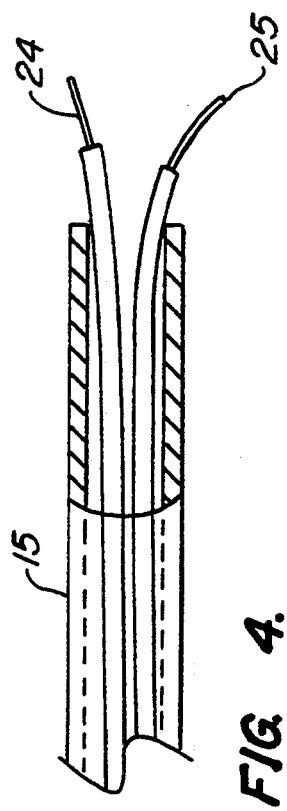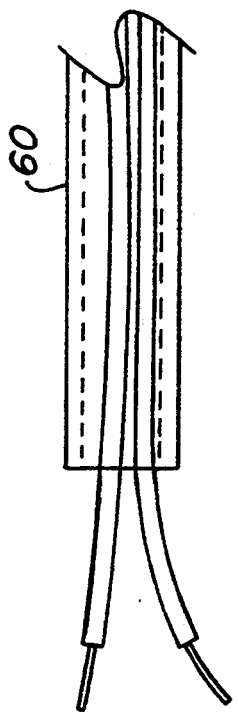
FIG. 4.
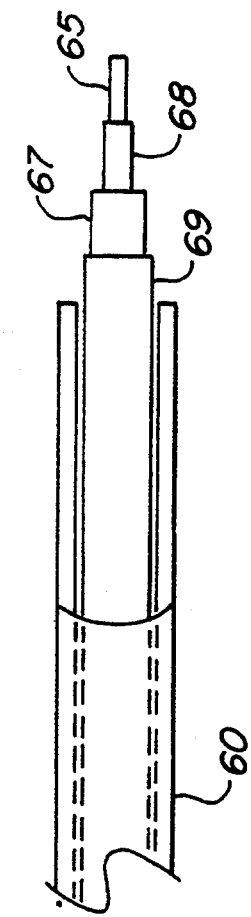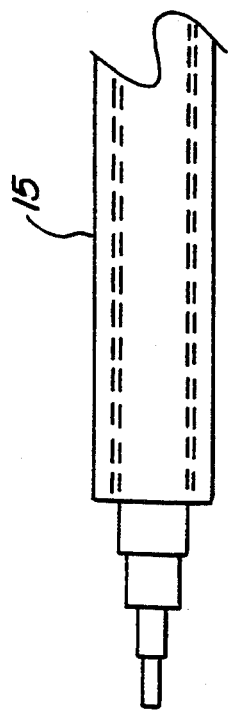
FIG. 5.

DRIVE SHAFT FOR AN INTRAVASCULAR CATHETER SYSTEM

BACKGROUND OF THE INVENTION

1. Field of the Invention

The present invention relates generally to drive shafts for use in intravascular catheter systems having working elements such as ultrasonic transducers or rotating cutting elements. More particularly, the present invention provides an improved drive shaft having a superior combination of column strength, rotational stiffness, flexibility and resistance to permanent deformation or kinking.

2. Description of the Background Art

Arteriosclerosis, also known as atherosclerosis, is a common human ailment arising from the deposition of fatty-like substances, referred to as atheromas or plaque, on the walls of blood vessels. Such deposits occur in both the peripheral blood vessels that feed the limbs of the body and the coronary vessels which feed the heart. When deposits accumulate in localized regions of a blood vessel, stenosis, or narrowing of the vascular channel, occurs. Blood flow is restricted and the person's health is at serious risk.

Numerous approaches for reducing and removing such vascular deposits are known, including balloon angioplasty, in which a balloon-tipped catheter is used to dilate a region of atheroma; atherectomy, in which a blade or cutting bit is used to sever and remove the atheroma; spark gap reduction, in which an electrical spark burns through the plaque; and laser angioplasty, in which laser energy is used to ablate at least a portion of the atheroma. In order to facilitate treatment of the stenosis, it is often desirable to obtain a visual image of the interior of the blood vessel within the region of interest Catheters having imaging elements such as ultrasonic transducers are often used to obtain these images.

In many cases, catheter systems having imaging or interventional devices will include a rotatable drive shaft disposed within the flexible catheter body. In imaging systems, the rotatable drive shaft will typically be connected to an ultrasonic transducer or to a movable mirror associated with an ultrasonic transducer.

An exemplary catheter system having a rotating ultrasonic transducer is disclosed in U.S. Pat. No. 4,794,931, the disclosure of which is incorporated herein by reference. In this system, a drive shaft disposed within a flexible tubular catheter body is used to rotate an ultrasonic transducer about an axis parallel to the catheter body. The ultrasonic transducer is thereby caused to scan a region of the blood vessel in a plane normal to the catheter body.

An alternative imaging catheter system is disclosed in co-pending U.S. patent application Ser. No. 08/006,224, filed on Jan. 19, 1993, the disclosure of which is incorporated herein by reference. In this embodiment, a drive shaft is connected to an ultrasonic transducer by a mechanical linkage which converts rotation of the drive shaft into pivotal oscillation of the transducer about an axis perpendicular to the long axis of the catheter body. The pivotal oscillation of the transducer causes the ultrasonic imaging beam to sweep back and forth through a plane to image a region forward of the distal end of the catheter body.

Another catheter system, which may include either an imaging or interventional work element connected to a rotating drive shaft, is disclosed in U.S. patent application Ser. No. 07/976,228, filed on Nov. 13, 1992, the disclosure of which is incorporated herein by reference. This "common lumen" catheter system includes a proximal region having multiple lumens for carrying guidewires or various work elements and a reduced profile single lumen distal region adapted to enter narrow and tortuous regions.

Drive shafts suitable for use in applications such as those described above must satisfy several demanding criteria, some of which conflict. First, a catheter drive shaft must have sufficient column strength to allow for advancement of the work element within the catheter by pushing the drive shaft from the proximal end. A drive shaft with inadequate column strength will tend to collapse or buckle. To provide adequate column strength, the drive shaft material should have a high elastic modulus.

Second, a rotating drive shaft must have adequate torsional rigidity. In the case of an ultrasonic transducer as an imaging element, the need for torsional rigidity is critical. An imaging catheter system typically includes equipment for displaying an image of the interior of the blood vessel. This display equipment is usually synchronized with the means for rotating the drive shaft, typically a drive motor connected to the proximal end of the drive shaft. For high quality imaging, the drive shaft must faithfully convert constant speed rotation of the motor into constant speed rotation of the imaging element. If the drive shaft twists or winds up on itself, the ultrasonic transducer will lose synchronization with the display equipment, and the displayed image may be blurred or degraded to the point of uselessness. For adequate torsional rigidity, the drive shaft material should have a high shear modulus.

Third, to allow for advancement of the work element into narrow and twisting regions of the patient's vascular system, at least a distal portion of the drive shaft should be reasonably flexible. This requirement is obviously at odds with the need for the drive shaft to have a high column strength. To address these conflicting requirements, some drive shafts are made in sections. Such a multiple section drive shaft would have a relatively stiff segment at its proximal end to allow for adequate pushability, and a relatively flexible segment at its distal end to allow bending for entry into narrow and tortuous regions.

Fourth, a rotating catheter drive shaft should be highly resistant to permanent deformation, or kinking, along its length. If a permanent bend develops in the drive shaft, the ultrasonic transducer will be subjected to a whipping action at the distal end of the catheter and uniform rotation of the imaging element will become impossible. This will drastically degrade the displayed image.

Finally, to the extent permitted by the other requirements, the drive shaft should have a small diameter to permit entry of the work element into and through narrow blood vessels, vessels which typically will have been even further narrowed by deposits of plaque on the vessel walls.

Past drive shafts have often been made of wound or braided wire cables. Some of these drive shafts have combined segments of varying flexibility, sometimes including a rigid metal member for stiffness at the proximal end. One such multiple segment drive shaft is disclosed in U.S. Pat. No. 5,108,411, the disclosure of which is incorporated herein by reference.

SUMMARY OF THE INVENTION

The present invention provides an improved drive shaft for rotating an imaging or interventional work element in an intravascular catheter system. In particular, the present invention provides a drive shaft, at least a section of which is formed of a material having superelastic properties. An alloy of nickel and titanium commonly known as nitinol has been found suitable for use in the present invention.

Superelasticity in metal alloys results from reversible austenite-martensite and martensite-martensite phase changes within the material. Upon loading, a phase change occurs when a critical level of stress and deformation is exceeded. Levels of strain that would result in permanent deformation in ordinary metals are fully recoverable in alloys having superelastic properties. In the context of the present invention, this allows the drive shaft to be flexed and bent quite severely without forming permanent kinks in the drive shaft.

In preferred embodiments, the drive shaft will be made in the form of a hollow tube. This allows the drive shaft to carry parallel conducting wires or coaxial conducting lines along the length of the shaft. These conducting means can carry electrical signals between an ultrasonic imaging transducer and associated control and display apparatus.

In another embodiment, a drive shaft is provided combining a relatively rigid proximal segment formed of a superelastic material with a relatively flexible distal segment formed of conventional wound wire strands.

BRIEF DESCRIPTION OF THE DRAWINGS

FIG. 4 depicts a drive shaft according to the present invention in which the superelastic section is in the form of a tubular member with parallel conducting wires disposed therein for conducting electrical signals along the length of the drive shaft;

FIG. 5 depicts a hollow drive shaft within which are disposed coaxial conducting lines for conducting signals along the length of the drive shaft;

DESCRIPTION OF SPECIFIC EMBODIMENTS

The present invention provides a drive shaft for use in a catheter system having a imaging or interventional work element. According to the present invention, at least a portion of the drive shaft will be formed of a material having superelastic properties. This superelastic material may be a nickel-titanium metal alloy commonly known as nitinol.

In preferred embodiments of the invention, the superelastic section of the drive shaft will be made in the form of a hollow tube so that wires or coaxial conducting lines may be disposed within the tube for conducting electric signals to and from the work element.

In some embodiments of the invention, the superelastic material will comprise only a portion of the complete drive shaft. Preferred embodiments of this type will have a proximal segment formed of the superelastic material and a distal segment formed of wound or braided wire strands. These embodiments will provide a desirable combination of stiffness at the proximal end and flexibility at the distal end.

Figure 1:
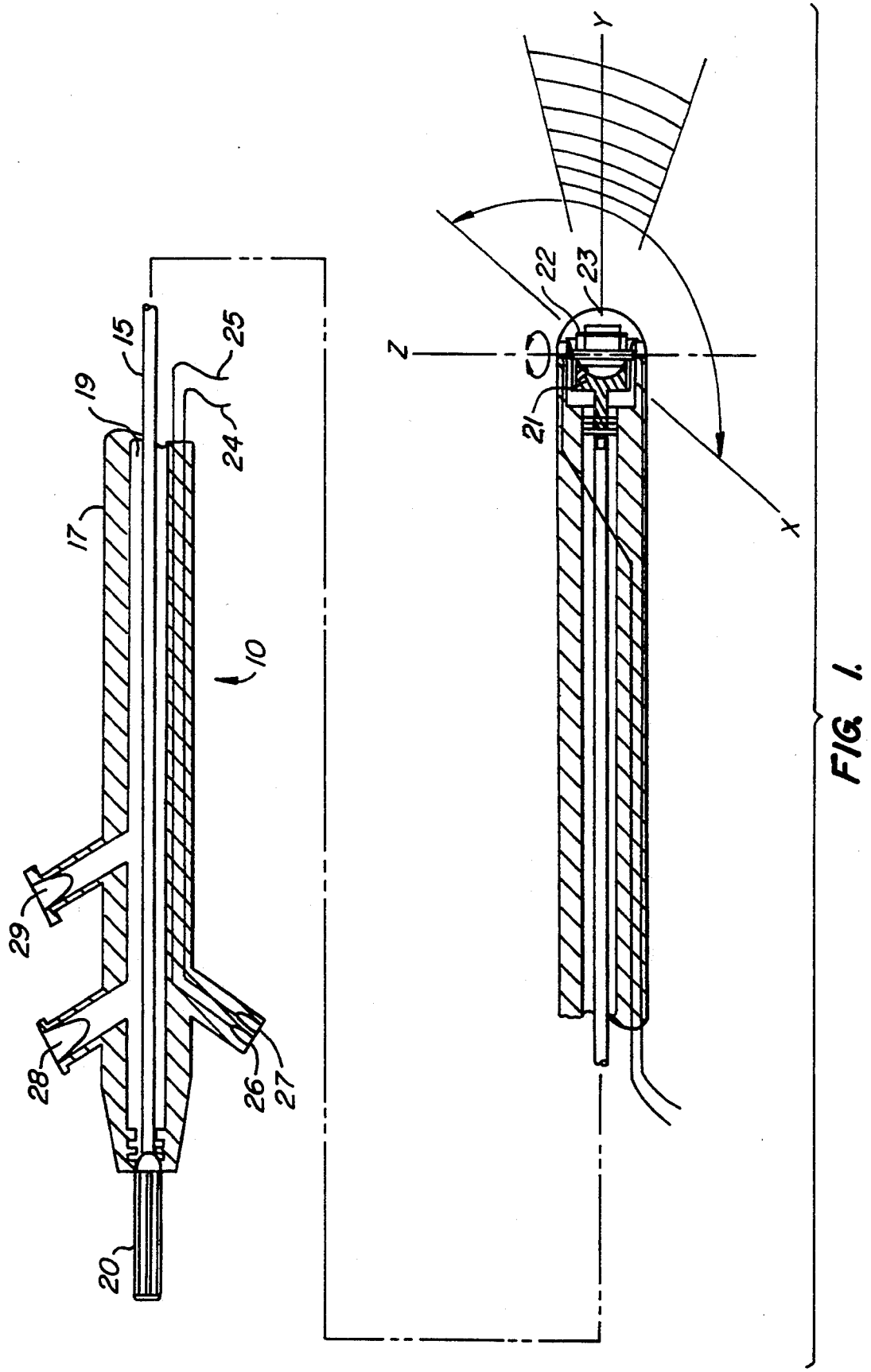
FIG. 1 depicts a forward viewing catheter system having a rotating superelastic drive shaft according to the present invention.

FIG. 1 is an illustration of a catheter system including a drive shaft 15 according to the present invention. The catheter system includes a flexible tubular member 17 with a central lumen 19. Drive shaft 15 is rotatably disposed within central lumen 19 of the flexible tubular member. End connecter 20 is fixed to the proximal end of the drive shaft for connecting the drive shaft to a drive motor (not shown)

In the embodiment depicted, drive shaft 15 is connected at its distal end to a mechanical linkage 21. In this embodiment, the mechanical linkage converts rotation the drive shaft into pivotal oscillation of a transducer holder 22 about the Z-axis shown. This causes ultrasonic transducer 23 to sweep back and forth through a segment of the X-Y plane, as shown.

Ultrasonic transducer 23 is electrically connected to control and display means (not shown) by conducting wires 24 and 25 through electrical connections 26 and 27. The catheter body is further provided with a fill port 28 and a drain port 29 for filling the central lumen with a fluid suitable for ultrasonic imaging and for flushing trapped air bubbles (which might interfere with imaging) out of the region of transducer 23.

The drive shaft will be described in more detail below. The remaining parts of the forward viewing catheter system, and particularly the mechanical linkage for converting rotation of the drive shaft into pivotal motion of the transducer, are described more fully in co-pending U.S. patent application Ser. No. 08/006,224, the disclosure of which has previously been incorporated herein by reference.

Figure 2:
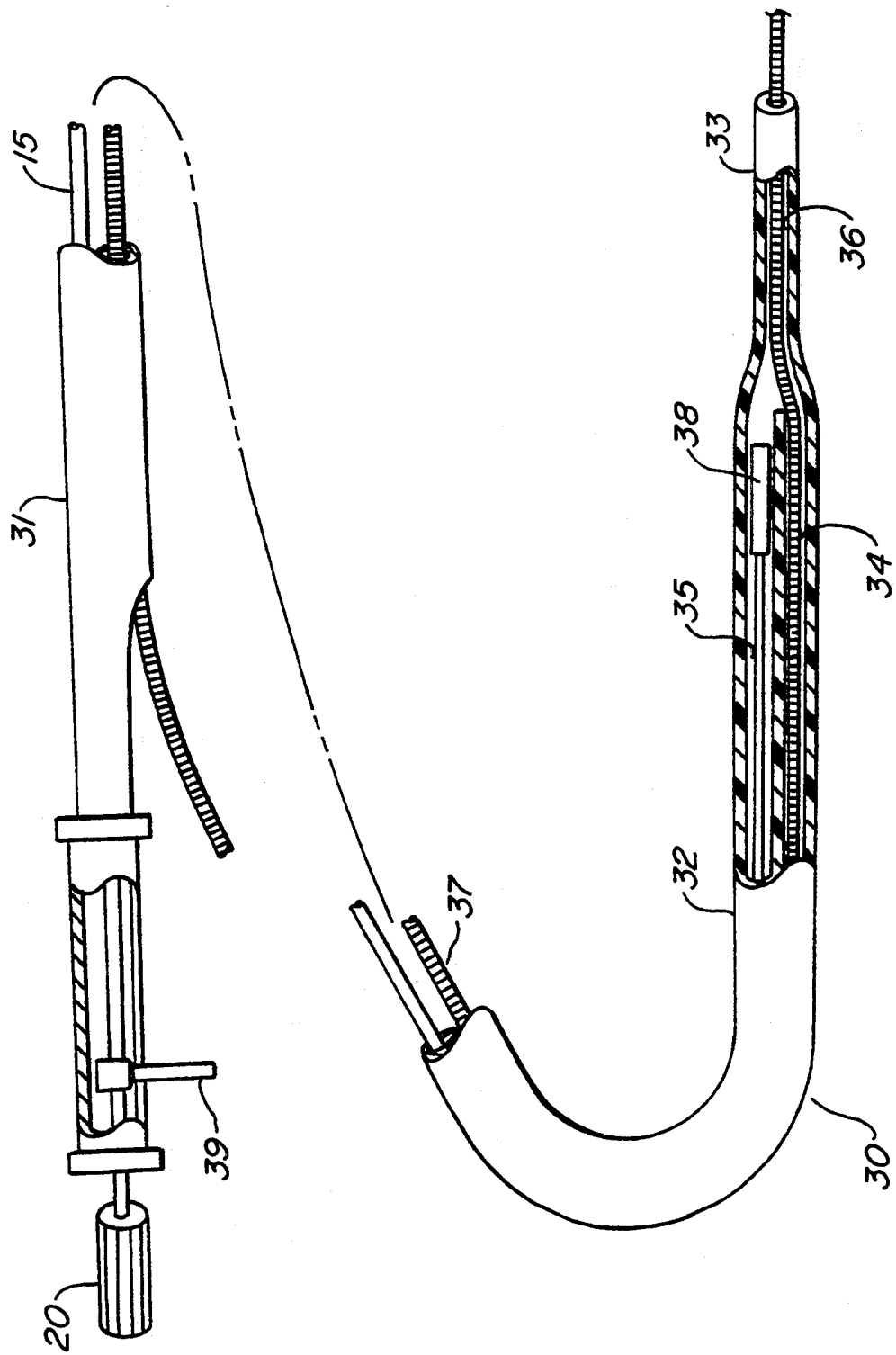
FIG. 2. depicts a common distal lumen catheter system having a rotating superelastic drive shaft according to the present invention.

FIG. 2 depicts a common lumen catheter system 30 having a drive shaft according to the present invention. In this embodiment, flexible member 31 has a proximal region 32 and a distal region 33. Proximal region 32 has at least two lumens, a guidewire lumen 34 and a work element lumen 35. Distal region 33 has a common lumen 36 connected to and in communication with both lumens of the proximal region.

In use, a guidewire 37 is first advanced into the patient's vascular system until it lies within the region of interest. The catheter system is then advanced into the patient by feeding the guidewire through common lumen 36 and directing it into guidewire lumen 34. Flexible member 31 is advanced into the patient until common lumen 36 lies within the region of interest. Guidewire 37 is then retracted into guidewire lumen 34 to clear common lumen 36. Work element 38, which will typically be an ultrasonic transducer but may be an interventional element, may then be advanced into common lumen 36 by moving handle 39 attached near the proximal end of drive shaft 15.

A common lumen catheter like that depicted in FIG. 2 is described more fully in co-pending U.S. patent application Ser. No. 07/975,769 and 07/976,228, both filed Nov. 13, 1992. The improved drive shaft depicted in FIG. 2 will be described more fully below.

In the embodiments depicted in both FIGS. 1 and 2, drive shaft 15 is a solid shaft formed of a material having superelastic properties. Typically, a drive shaft according the present invention will be made of nitinol, an alloy of nickel and titanium.

Superelastic materials (including nitinol) are unlike conventional materials in that they may undergo large amounts of deformation without suffering permanent, or plastic, deformation. This characteristic is known as superelastic, or pseudoelastic, behavior. This superelastic behavior is depicted graphically in FIGS. 3A and 3B.

Figure 3A:
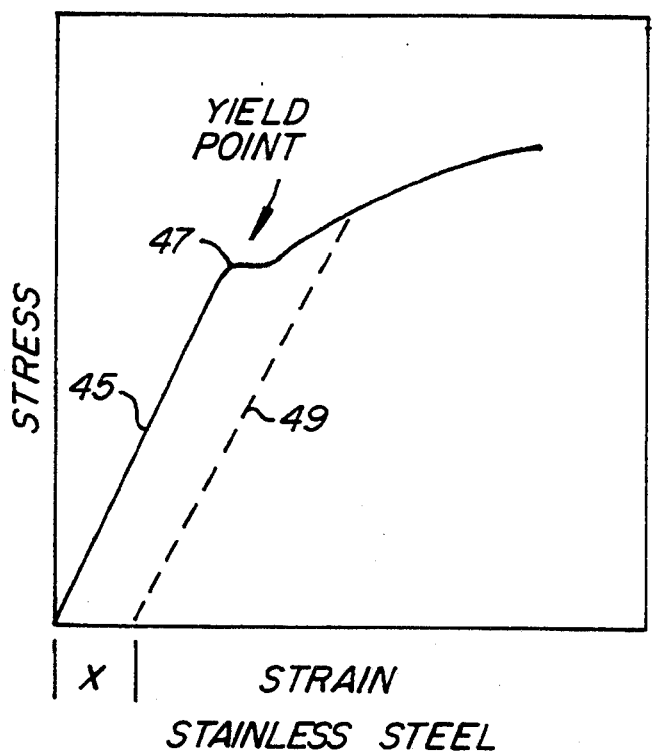
FIGS. 3A and 3B are illustrative stress-strain curves for loading and unloading of conventional and superelastic materials.

FIG. 3A is a typical stress-strain curve for a conventional metal such as a stainless steel which might be used as a drive shaft in a catheter system. A stress-strain curve like this is obtained by placing a wire sample in the movable jaws of a conventional tensile testing apparatus. A load cell measures the force on the movable jaws (and hence on the wire). That force is plotted on the y-axis of the graph. The jaws are set to move apart at a constant rate, thus providing a constant rate of strain. That strain is measured along the x-axis.

As the sample is loaded, stress within the material increases along the constant-slope region 45 of the solid portion of the curve. The strain in this region is reversible and is known as elastic deformation. Elastic deformation results from changes in spacing between individual atoms within the material. If the load were removed from the sample at this time, the atoms would return to their normal distances, the elastic deformation would reverse itself, and the material would return to its original shape and size.

As loading continues however, the material reaches a yield point 47. Atoms begin to "slip" in crystalline planes past one another, and permanent plastic deformation occurs. Once a conventional material has reached its yield point, unloading will result in the reversal of elastic deformation, but plastic deformation will remain and the shape of the material will have been permanently changed.

The dashed portion 49 of the curve of FIG. 3A represents unloading of a sample loaded past its yield point. A wire sample stretched past its yield point will be permanently increased in length by an amount shown as x in FIG. 3A. A catheter drive shaft bent past its yield point will retain a permanent bend which can substantially hinder its ability to transmit torque reliably from the drive motor to the work element.

Figure 3B:
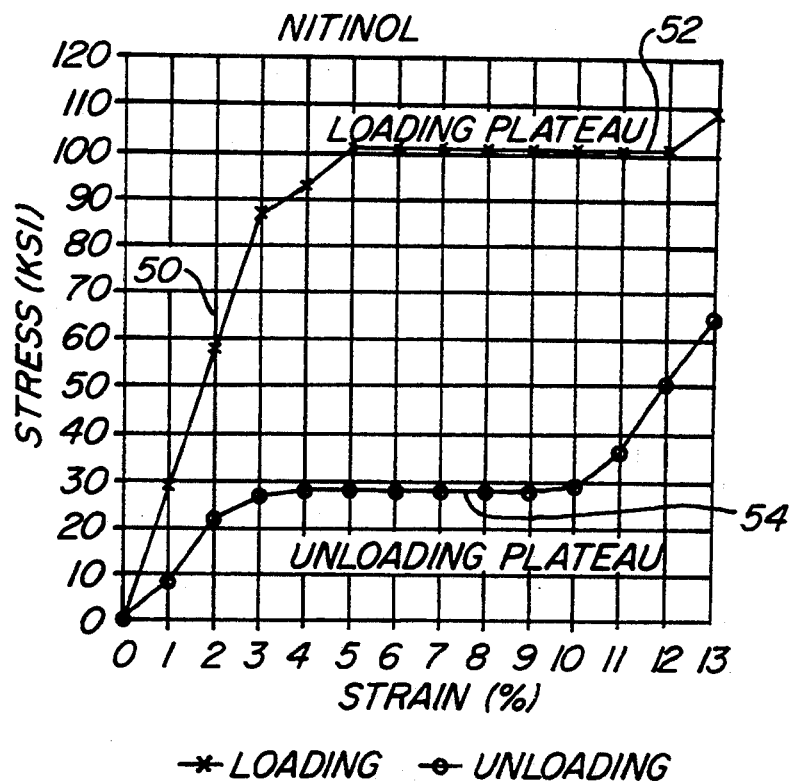

In contrast, FIG. 3B is a stress-strain curve for a superelastic material. Similar to the conventional material, a superelastic material will first experience elastic deformation within the region of constant slope 50. Such a material behaves very differently at its "yield point" however. Instead of atomic planes slipping past one another, increasing strain is accommodated by a one or more phase changes within the material. This occurs over the region shown as the area 52 labeled "loading plateau" in FIG. 3B. Within this region, increasing strain can be accommodated without increasing the level of stress within the material.

Upon unloading, the elastic deformation is reversed as in the conventional material. In addition, the phase change reverses itself through the region 54 labeled "unloading plateau" in FIG. 3B. The material returns to its original shape, even after experiencing a strain level well in excess of that which would have permanently deformed a conventional material. In the context of a catheter system, a superelastic drive shaft made of nitinol may be bent quite severely without forming permanent bends or kinks in the shaft.

In some embodiments of the invention, drive shaft 15 will be formed in the shape of a hollow tube 60, as shown in FIG. 4. The hollow tube will generally have an outside diameter in the range of 0.100 to 0.008 inches and an inside diameter in the range of 0.090 to 0.004 inches. More commonly, the outside and inside diameters will be in the ranges of 0.030 to 0.014 inches and 0.024 to 0.008 inches.

In a preferred embodiment, the hollow tube is a superelastic nitinol tube having an outside diameter of about twenty-one one-thousandths of an inch and an inside diameter of about sixteen one-thousandths of an inch. These dimensions provide sufficient stiffness and torsional rigidity to allow for adequate pushability and torque transmission to an ultrasonic transducer at the distal end. Additionally, the inside diameter of such a tube is large enough to accommodate conducting wires 24 and 25 for carrying electrical signals between the transducer and the control and display equipment. Nitinol tubing of this size is available in specially manufactured custom lots from at least the following sources:

1) Innovative Technology International, Inc., Beltsville, Md.;
2) Raychem Corporation, Menlo Park, Calif.; and
3) Shape Memory Applications, Inc., Sunnyvale, Calif.

Conducting wires 24 and 25 may be disposed substantially parallel as shown in FIG. 4. Of course, wires 24 and 25 may also be twisted around each other to form a twisted wire pair. Alternatively, coaxial conducting lines may be used as depicted in FIG. 5. In this embodiment, first and second conducting lines 65 and 67 are separated from one another and from the body of the drive shaft 15 by insulating layers 68 and 69.

Figure 6:
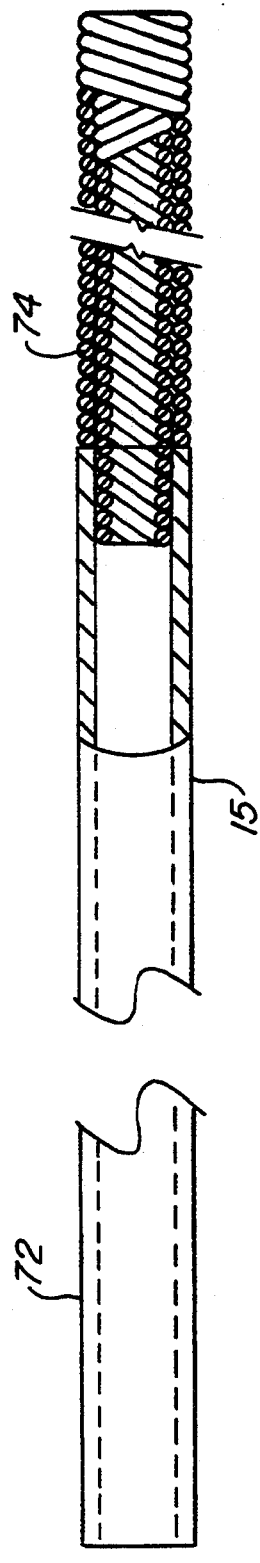
FIG. 6 depicts a drive shaft which includes a relatively stiff proximal segment formed of a superelastic material and a more flexible distal segment formed of wound wire strands.

In some applications it will be desirable to combine a section of superelastic material with a section of braided or wound wire strands to form a drive shaft having segments of differing flexibility as shown in FIG. 6. The drive shaft 15 depicted therein has a proximal segment 72 formed of a superelastic tube and a more conventional wound wire distal segment 74. The wound wire distal section is more fully described in U.S. Pat. No. 5,108,411, the disclosure of which has previously been incorporated by reference.

Figure 7:
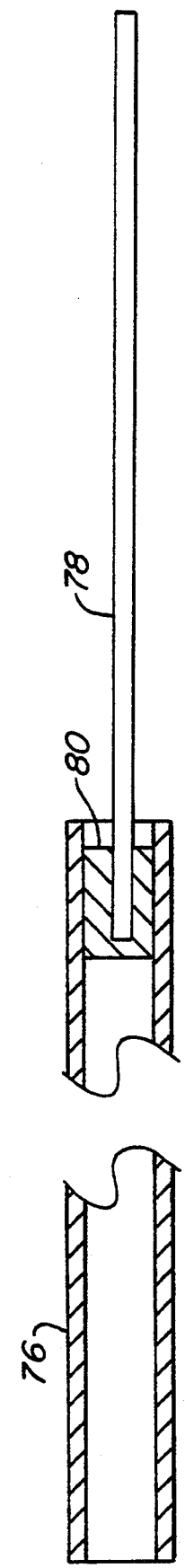
FIG. 7 depicts a drive shaft which includes a relatively rigid large diameter proximal segment and a relatively flexible small diameter distal segment.

Alternatively, a composite drive shaft having segments of varying flexibility may be constructed from superelastic tubular members of varying diameter as shown in FIG. 7. This embodiment includes a proximal segment 76 of relatively large diameter and a distal segment 78 of a relatively smaller diameter. The two segments may be joined in any suitable manner. In the embodiment depicted, the small diameter segment 78 is set into a plug 80 fixed within large diameter segment 76. Alternate joint configurations could obviously be used as well. It should be noted that the individual pieces will preferably be force fit or mechanically locked to one another or held by another means such as epoxy. Ordinary soldering and brazing techniques are ineffective with nitinol alloys.

The embodiments depicted in FIGS. 6 and 7 each include relatively rigid proximal segments and relatively flexible distal segments. These embodiments achieve superior pushability and torque transmission in the proximal segments. Simultaneously, the flexibility of the distal segments permit entry of the work element into narrow and twisting regions of the patient's vascular system. Depending on the specific application, the flexible distal segment will commonly comprise from one percent to thirty percent of the overall catheter length.

Although the foregoing invention has been described in detail for purposes of clarity of understanding, certain modifications will be obvious to those skilled in the art. Thus, the scope of the invention should be construed with reference to the appended claims including the full range of equivalents to which the inventor is entitled.

What is claimed is:

1. An improved catheter system of the type having a work element and a rotatable drive shaft, wherein the improvement comprises forming the drive shaft at least in part from a material having superelastic properties, wherein the drive shaft includes means for coupling to a drive motor at its proximal end and the work element at its distal end.

2. The drive shaft of claim 1, wherein the superelastic material is a metal alloy including nickel and titanium.

3. The drive shaft of claim 1, wherein the drive shaft comprises an elongate member in the form of a tube.

4. The catheter system of claim 1, wherein the work element is an ultrasonic transducer.

5. A catheter system comprising:
   a catheter body comprising a flexible member having a lumen extending therethrough;
   a drive shaft comprised at least in part of a material having superelastic properties and having a proximal end and a distal end and comprising an elongate tubular member rotatably disposed within the lumen of the catheter body;
   a work element coupled to the drive shaft and;
   means for coupling to a drive motor at the proximal end of the drive shaft.

6. The catheter system of claim 5, wherein the work element comprises an ultrasonic transducer.

7. The catheter system of claim 5, further comprising:
   means for conducting electricity disposed within the drive shaft and electrically connected to the work element.

8. The catheter system of claim 7, wherein the conducting means comprises a plurality of conducting wires disposed within the drive shaft.

9. The catheter system of claim 7, wherein the conducting means comprises coaxial conducting lines disposed within the drive shaft.

10. The catheter system of claim 5, wherein the drive shaft is formed of a superelastic material.

11. The catheter system of claim 10, wherein the superelastic material is nitinol.

12. A drive shaft for rotating a work element in a catheter system, the drive shaft comprising:
   a first segment formed of a superelastic material and having means for connecting to a drive motor attached to a proximal end thereof; and
   a second segment connected to a distal end of the first segment.

13. The drive shaft of claim 12, wherein the superelastic material is a metal alloy including nickel and titanium.

14. The drive shaft of claim 12, wherein the second segment is more flexible than the first segment.

15. The drive shaft of claim 14, wherein the second segment is formed of a superelastic material.

16. The drive shaft of claim 15, wherein the second segment has a diameter less than that of the first segment.

17. The drive shaft of claim 14, wherein the second segment comprises wound wire.

18. An improved catheter system of the type comprising: a tubular member having a proximal end and a distal end wherein the tubular member includes a proximal region having at least two lumens and a distal region having a single lumen which is connected to and in communication with said two lumens and which has a cross-sectional area less than the combined cross-sectional area of the two lumens of the proximal region; a work element disposed within the tubular member; and a rotatable drive shaft connected to the work element; wherein the improvement comprises forming at least a portion of the drive shaft from a superelastic material, wherein the drive shaft includes means for coupling to a drive motor at its proximal end and the work element at its distal end.

* * * * *